US006887862B2

(12) United States Patent
Rychnovsky

(10) Patent No.: US 6,887,862 B2
(45) Date of Patent: May 3, 2005

(54) METHOD FOR IMPROVING TREATMENT SELECTIVITY AND EFFICACY USING INTRAVASCULAR PHOTODYNAMIC THERAPY

(75) Inventor: Steven J. Rychnovsky, Santa Barbara, CA (US)

(73) Assignee: Miravant Systems, Inc., Santa Barbara, CA (US)

( * ) Notice: Subject to any disclaimer, the term of this patent is extended or adjusted under 35 U.S.C. 154(b) by 0 days.

(21) Appl. No.: 09/871,441

(22) Filed: May 31, 2001

(65) Prior Publication Data

US 2002/0183301 A1 Dec. 5, 2002

(51) Int. Cl.$^7$ ...................... A61K 31/33; A61K 31/555; A61K 31/40; A61K 31/35; A61N 5/067

(52) U.S. Cl. ...................... 514/183; 514/185; 514/410; 514/455; 514/461; 604/89

(58) Field of Search .................................. 424/9.6, 9.61; 514/183, 185, 410, 455, 461; 607/89

(56) References Cited

U.S. PATENT DOCUMENTS

| | | | |
|---|---|---|---|
| 5,116,864 A | | 5/1992 | March et al. |
| 5,308,861 A | | 5/1994 | Aizawa et al. |
| 5,354,774 A | | 10/1994 | Deckelbaum et al. |
| 5,514,707 A | | 5/1996 | Deckelbaum et al. |
| 5,620,438 A | | 4/1997 | Amplatz et al. |
| 5,833,682 A | | 11/1998 | Amplatz et al. |
| 5,964,751 A | | 10/1999 | Amplatz et al. |
| 6,054,449 A | * | 4/2000 | Robinson et al. ........... 514/185 |
| 6,071,944 A | | 6/2000 | Rodgers et al. |
| 6,132,423 A | | 10/2000 | Aita et al. |

FOREIGN PATENT DOCUMENTS

| | | |
|---|---|---|
| WO | WO 01/24825 | 4/2001 |
| WO | WO 01/24825 A2 | 4/2001 |
| WO | WO 01/35997 A2 | 5/2001 |
| WO | WO 01/35997 | 5/2001 |

OTHER PUBLICATIONS

Isaac Nyamekye, et al., Photodynamic Therapy of Normal and Balloon–Injured Rat Carotid Arteries Using 5–Amino–Levulinic Acid (journal), American Heart Association, Inc., Dec. 15, 1995, pp. 417–425, vol. 91, No. 2.
Motoya Hayase, et al., Photoangioplasty With Local Motexafin Lutetium Delivery Reduces Macrophages in a Rabbit Post–Balloon Injury Model (journal), Cardiovascular Research, 2001, pp. 449–455, vol. 49.
Glenn M. Lamuraglia, et al., Chloroaluminum Sulfonated Phthalocyanine Partitioning in Normal and Intimal Hyperplastic Artery in the Rat, Implications for Photodynamic Therapy (journal), American Journal of Pathology, Dec. 28, 1992, pp. 1898–1905, vol. 142, No. 6.

Yukari Yasunaka, et al., In Vivo Accumulation of Photosensitizers in Atheroslerotic Lesions and Blood in Atherosclerotic Rabbit (journal), Lasers in the Life Sciences, 1991, pp. 53–65.
J. P. Savary, et al., Photodynamic Therapy of Early Squamous Cell Carcinomas of the Esophagus: A Review of 31 Cases (journal), Georg Thieme Verlag Stuttgart, Endoscopy, 1998, pp. 258–265, vol. 30.
J. H. Kinsey, et al, Photodynamic Effect of Hematoporphyrin Derivative as a Function of Optical Spectrum and Incident Energy Density (journal), Cancer Research, Dec. 1981, pp. 5020–5026, vol. 41.
CancerLinksUSA, Cancer Treatment: Photodynamic Therapy (website article), Aug. 24, 1999.
DUSA Pharmaceuticals, Inc/Berlex Laboratories, Inc., Novel Therapy Receives FDA Approval for Treatment of Common Skin Lesions (website article), 9/27, Publication date not available).
Levulan (registered trademark) Kerastick (registered trademark) (aminolevulinic acid HCl) for Topical Solution, 20% (advertisement), 2000.
G. Michael Vincent, et al., Effects of Benzoporphyrin Derivative Monoacid on Balloon Injured Arteries in a Swine Model of Restenosis (journal), SPIE, pp 72–77, vol. 2671, (publication date not available).
C. A. Waters, et al., Photodymic Therapy with the New Photosensitizer Drug MV6401 Prevents Neointima Formation in Balloon–Injured Rat Carotid Arteries (journal), Supplement to Circulation, Abstracts from Scientific Sessions 2000, Nov. 12, 2000, p 423, vol. 102, No. 18.
I. M. Leitch, et al., Photodymic Therapy with the New Photosensitizer Drug, MV6401, Results in Targeted Cell Death of Neo–Intimal Lesions in Rat Arteries (journal), Supplement to Circulation, Abstracts from the 72nd Scientific Sessions, Nov. 7, 1999, p 247, vol. 100, No. 18.
S. G. Rockson, et al., Photoangioplasty: An Emerging Clinical Cardiovascular Role for Photodynamic Therapy (journal), Circulation, Aug. 1, 2000, pp 591–596, vol. 102.
P. Ortu, et al., Treatment of Arterial Intimal Hyperplasia with Photodymanic Therapy (journal), Photodynamic Therapy and Biomedical Lasers, 1992, pp 225–232.
D. Eton, et al., Inhibition of Intimal Hyperplasia by Photodynamic Therapy Using Photofrin (journal), Journal of Surgical Research, 1992, pp 558–562, vol. 53, No. 6.
M. P. Jenkins, et al., Reduction in the Response to Coronary and Iliac Artery Injury with Photodynamic Therapy Using 5–Aminolaevulinic Acid (journal), Cardiovascular Research, 1999, pp 1–8, 1.

(Continued)

Primary Examiner—Raymond J. Henley, III
(74) Attorney, Agent, or Firm—Bryan Cave LLP

(57) ABSTRACT

A method in which photodynamic therapy is employed to inhibit, stabilize or reduce occlusions within the cardiovascular system by utilizing light within the spectral region of approximately 390 to approximately 610 nm.

59 Claims, 15 Drawing Sheets

OTHER PUBLICATIONS

P. Gonschior, et al., Endovascular Catheter–Delivered Photodynamic Therapy in an Experimental Response to Injury Model (journal), Basic Res Cardiol, 1997, pp. 310–319, vol. 92.

G. M. Lamuraglia, et al., Photodynamic Therapy of Vein Grafts: Suppression of Intimal Hyperplasia of the Vein Graft But Not the Anastomosis (journal), Journal of Vascular Surgery, Jun. 1995, vol. 21, No. 6.

G. M. Lamuraglia, et al., Photodynamic Therapy Inhibition of Experimental Intimal Hyperplasia: Acute and Chronic Effects (journal), Journal of Vascular Surgery, 1994, pp. 321–331, vol. 19, No. 2.

Hugh L. Narciso, et al., Retention of Tin Ethyl Etiopurpurin (SnET2) by Atheromatous Plaques: Studies in Vitro & In Vivo Rabbit (journal), SPIE, pp. 30–41, vol. 2130, (publication date not available).

* cited by examiner

| Wavelength (nm) | Drug Dose (μmol/kg) | Light Dose (J) | Treatment Time (Post-Injection) | Max. Acell. (%) | Sur. Tissue Damage |
|---|---|---|---|---|---|
| 665 | 0.1 | 106 | 4 hr | 0 | > 3 |
| 532 | 2.0 | 135 | 4 hr | 60 | 2 |
| 514 | 2.0 | 137 | 4 hr | 70 | 2 |
| 458 | 1.0 | 137 | 4 hr | 57 | 2 |
| 442 | 1.0 | 125 | 4 hr | 88 | 1.5 |

Fig. 9

| Drug | Wavelength (nm) | Drug Dose | Light Dose (J) | Treatment Time (Post-Injection) | Max. Acell. (%) | Sur. Tissue Damage |
|---|---|---|---|---|---|---|
| BPD-MA (benzoporphyrin) | 458 | 2 μmol/kg | 137 | 4 hr | 60 | 2 |
| LuTex (texaphrin) | 458 | 4.5 mg/kg | 300 | 24 hr | 40 | 2 |
| Rose Bengal 00902 (xanthene) | 580 | 5 μmol/kg | 80 | 8 hr | 43 | 2-3 |
| MV6401 (chlorophyll) | 458 | 1.0 μmol/kg | 137 | 4 hr | 57 | 2 |
| MV970205 (benzochlorin) | 458 | 1.0 μmol/kg | 80 | 4 hr | 37 | 2 |
| MV000602 (porphyrin) | 532 | 1.0 μmol/kg | 138 | 4 hr | 90 | 2 |

Fig. 10

METHOD FOR IMPROVING TREATMENT SELECTIVITY AND EFFICACY USING INTRAVASCULAR PHOTODYNAMIC THERAPY

FIELD OF THE INVENTION

The present invention relates generally to a method in which photodynamic therapy is employed to inhibit, stabilize or reduce occlusions within the cardiovascular system of the body.

BACKGROUND OF THE INVENTION

Occlusive events of the cardiovascular system constitute a significant area of medical need for which current treatment modalities are inadequate. Examples of occlusive events include restenosis following stenting or angioplasty procedures, formation of occlusions either within or in the proximity of vascular grafts, atherosclerosis, negative remodeling following cardiovascular interventions and stenosis resulting from vascular injury. In each of these events, a reduction in the vessel lumen occurs, often as the result of plaque formation or cell proliferation, which causes a partial or complete occlusion of the vessel lumen. Therefore, the treatment objective in each case is to provide a means for inhibition, stabilization or reduction of such occlusive events within the cardiovascular system of the body.

A wide variety of treatment strategies have been investigated for the treatment of these conditions, including pharmacological drug therapy, bypass surgery, percutaneous angioplasty, mechanical stents, drug coated stents, lasers, atherectomy devices, ultrasound, cryotherapy and ionizing radiation. While each of these show some promise, significant limitations exist with each. The reasons for these limitations, while too numerous to mention here, are well known in the art.

Consequently, there exists a need for better methods of treatment of cardiovascular disease indications. In particular, a therapy is desired which provides a beneficial means for treating a localized region of a vessel or graft without causing systemic toxicities, damage to surrounding tissues or local injury of the vessel. Furthermore, it is desirable to provide a therapy whose primary mechanism of action does not rely on the induction of DNA damage.

One therapy that has recently been investigated for the treatment of these indications is Photodynamic Therapy (PDT). PDT is a relatively new modality that is under development for the treatment of such conditions as malignancies, locally diseased tissues, hyperproliferating tissues, pathogens and certain unwanted normal tissues. The PDT procedure is conducted by administering a photosensitizing drug to the desired treatment zone, by either local or systemic means, followed by exposure to photoactivating light. During a PDT procedure, a photoactivating light excites the photosensitizer drug that causes modification or destruction of tissue, which is the desired clinical effect.

In the case of systemic administration, photosensitizers accumulate to varying degrees within tissues depending on the pharmacokinetic and distribution profile of the photosensitizer and the target cell types comprising the tissues. Given this, key factors to be considered in selecting a photosensitizer drug for systemic administration are uptake and selectivity in the target tissue. In general, a significant amount of drug screening is conducted in order to identify a compound that has the appropriate uptake in the target tissue, while having limited uptake in the surrounding tissue that is not the target of the treatment. The chemical factors that enable certain photosensitizers to accumulate to a greater degree at a target site are not well understood. In addition, the biological factors that result in the preferential uptake of some photosensitizers in certain tissue types compared to others are not well understood. It is the prevailing view throughout the scientific community, however, that each photosensitizer has its own distribution and pharmacokinetic properties within different tissues and these properties can play a significant role in the relative usefulness of a drug for use in PDT. These properties of preferential uptake in target tissue have been utilized to date to provide the selectivity associated with PDT.

In the case of local drug administration, systemic uptake and distribution are considered to be less important. This view is based on the perception that the uptake kinetics are different in this case, being determined by the characteristics of the particular drug and the local drug delivery device. Furthermore, in the case of local drug administration, selectivity is generally viewed as being less important since the photosensitizer is delivered directly to the desired treatment site rather than to the surrounding tissues that are not the target of the treatment. In other words, the primary purpose of utilizing local drug delivery is to deliver a higher dose of drug to the target site than is delivered to the non-target tissues, thereby providing a selective treatment. An additional advantage of local administration is the possibility of using a lower total drug dose by selectively delivering the drug directly to the target tissue rather than systemically throughout the entire body.

Various photosensitizers have been investigated for treatment of cardiovascular disease indications. These include Photofrin (D. Eton, et al., Inhibition of Intimal Hyperplasia by Photodynamic Therapy Using Photofrin, J Surg Res, 53, 558–62, 1992), 5-Aminolaevulinic Acid (M. P. Jenkins, et al., Reduction in the Response to Coronary and Iliac Artery Injury with Photodynamic Therapy Using 5-Aminolaevulinic Acid, Cardiovascular Res, 1, 1–8, 1999), tin ethyl etiopurpurin, Visudyne® (G. M. Vincent, et al., Effects of Benzoporphyrin Derivative Monoacid on Balloon Injured Arteries in a Swine Model of Restenosis, SPIE vol 2671, 72–77, 1996), Antrin®, (S. G. Rockson, et al., Photoangioplasty: An Emerging Clinical Cardiovascular Role for Photodynamic Therapy, Circulation, 102, 591–96, 2000), phthalocyanines (P. Ortu, et al., Treatment of Arterial Intimal Hyperplasia with Photodynamic Therapy, Photodynamic Therapy and Biomedical Lasers, Elsevier Science Publishers, edited by P. Spinella, et al, 1992) and MV6401 (I. M. Leitch, et al., Photodynamic Therapy with the New Photosensitizer Drug MV6401 Prevents Neointima Formation in Balloon-Injured Rat Carotid Arteries, *Circulation*, (Suppl. II), Vol 102, No. 18, Abstr. 2059, p. II-423., 2000; C. A. Waters, et al., Photodynamic Therapy with the New Photosensitizer Drug, MV6401, Results in Targeted Cell Death of Neo-Intimal Lesions in Rat Arteries, Circulation, (Suppl. II), Vol. 102, No. 18, Abstr. 1208, p. II-247, 2000).

In the case of inhibition of neointima formation, a significant number of animal studies have been conducted to investigate the usefulness of PDT. These studies have used light at wavelengths of 630 nm and greater, employing both systemic and local drug delivery (P. Gonschior, et al., Endovascular Catheter-Delivered Photodynamic Therapy in an Experimental Response to an Injury Model, Basic Res Cardiol, 92, 310–19, 1997; D. Eton, et al., Inhibition of Intimal Hyperplasia by Photodynamic Therapy Using Photofrin, J Surg Res, 53, 558–62, 1992; S. G. Rockson, et al., Photoangioplasty: An Emerging Clinical Cardiovascular Role for Photodynamic Therapy, Circulation, 102, 591–96, 2000), and using both intravascular and external light delivery schemes.

Other studies have investigated the inhibition of neointima formation in natural vein grafts in which, prior to implantation, the graft receives a PDT treatment using 675 nm light (G. M. LaMuraglia, et al., Photodynarnic Therapy of Vein Grafts: Suppression of Intimal Hyperplasia of the Vein Graft but not the Anastomosis, J Vascular Surg, 21, 1995). Still further studies have investigated the reduction or stabilization of plaques in diseased artery animal models using a photosensitizer delivered systemically and excited with either external or intravascular light with a wavelength near 730 nm. These studies led to the application of PDT in human clinical trials using Lutetium texaphyrin (LuTex) in combination with a laser source having a wavelength near 730 nm (S. G. Rockson, et al., Photoangioplasty: An Emerging Clinical Cardiovascular Role for Photodynaniic Therapy, Circulation, 102, 591–96, 2000). These human clinical trials have two primary efficacy endpoints: inhibition of restenosis following angioplasty based interventions and reduction/stabilization of plaques in atherosclerotic lesions.

Although wavelengths of 630 nm and greater were utilized in the aforementioned studies, for each of the drugs listed above, the strongest absorption feature actually occurs at wavelengths less than 610 nm. Therefore, each of these drugs should be more efficient when using wavelengths less than 610 nm, as opposed to the red/infrared wavelengths that were actually used in these studies. Wavelengths of 630 nm and greater are referred to herein as red/infrared. Wavelengths less than approximately 630 nm roughly correspond to the other colors in the spectrum, e.g., orange, yellow, green, blue, etc. In fact, in every cardiovascular PDT investigation to date, excitation wavelengths of 630 nm or greater have been used, even though these do not provide the most efficient means of excitation.

The major advantage of using wavelengths greater than 630 nm is associated with the absorption of light by the hemoglobin in blood. Specifically, for wavelengths generally greater than 630 nm, absorption by hemoglobin is minimized, allowing these wavelengths to readily penetrate through blood. This reduces the need for exclusion of blood from the region between the light delivery device and the tissue to be treated, allowing the use of relatively simple light delivery devices. For example, S. G. Rockson, et al., Photoangioplasty: An Emerging Clinical Cardiovascular Role for Photodynamic Therapy, Circulation, 102, 591–96, 2000, has pointed out that the ideal photosensitizer for cardiovascular PDT should display maximal absorption in the range of 700–800 nm or 950–1100 nm. They have further stated the efficacy of their approach can be attributed to the selective uptake of their photosensitizer and the deep penetration of light through blood and tissue that is achievable at their longer 732 nm excitation wavelength.

On the other hand, the relatively deep light penetration in tissue for wavelengths of 630 nm and greater could lead to PDT-induced damage of surrounding tissues. Of course, this would only be the case if the photosensitizer does not have sufficient selectivity to the target tissue. However, given the use of local drug delivery and in the case of systemic administration, the perceived highly selective nature of photosensitizers, other studies have given little or no attention to the risk associated with PDT-induced damage of surrounding tissues.

A third factor that has led researchers to rely on wavelengths greater than 630 nm is based on the geometric falloff of light emitted from a cylindrical or point source. As light radiates outward from either a cylindrical source or a point source, it must decrease in intensity since it is gradually spread over an ever-increasing volume. This conclusion is a result of basic physics and is simply a consequence of the law of conservation of energy. Furthermore, even in the red/infrared portion of the spectrum, light undergoes relatively strong absorption and scattering by tissue. Therefore, in addition to the geometric falloff, both absorption and scattering limit the penetration depth of light into surrounding tissues, even in the red/infrared portion of the spectrum. The combination of this, along with the previously mentioned factors, has led to the exclusive use of wavelengths of 630 nm and greater in cardiovascular PDT studies to date.

While the perceived advantages of using red/infrared light in cardiovascular PDT treatment may appear sound, this view does not take into account the unexpected result that the sensitivity of surrounding tissues to the PDT effect is often greater than that of the target tissues. We have discovered that, even while accounting for the apparently high relative drug uptake in the target tissue achieved with either systemic or local drug administration and the rapid attenuation of red/infrared light generated from an intravascular cylindrical diffuser, unacceptably high PDT damage occurs beyond the target tissue before the therapeutic threshold is reached in the target tissue. The reasons behind this unexpected result cannot be definitively established due to the complexity of the model and the PDT interaction. However, it may be due to a combination of the penetration depth of red/infrared light and a relatively higher sensitivity of surrounding tissue to the PDT effect. This sensitivity may be due to a tendency of some photosensitizers to localize in more critical regions within cells of surrounding tissues or a tendency to cause shut down of critical vasculature or nerves in these tissues. Alternatively, the assumption of high localization, especially with systemic administration, is often based on the relative brightness observed using fluorescence microscopy. However, this may not necessarily be correct since phenomena such as fluorescent quenching can lead to erroneous conclusions with fluorescence microscopy. Furthermore, even more accurate measurement techniques, such as high pressure liquid chromatography (HPLC) or autoradiography do not provide significant information on cell binding sites or intracellular location.

We have discovered that photosensitizer selectivity alone is insufficient to ensure minimal damage to surrounding tissue while simultaneously providing the desired level of efficacy within the targeted cardiovascular tissue. A wide variety of tissue types, such as myocardium, lung, nerves, adjacent vessels, fat, etc. are typically located near target vessels. In practice, it is nearly impossible for a drug to have the necessary preferential uptake characteristics in the target tissue, while not being taken up to some degree in these surrounding tissues as well. We have found that in situations where such surrounding tissues contain some amount of the photosensitizer, there is an especially difficult challenge in the practical implementation of PDT using red/infrared light. Penetration of light in this wavelength range appears to cause undesired PDT treatment in important underlying tissues that are well beyond the desired treatment zone of the vessel, thereby making it difficult to control treatment depth. Furthermore, while in theory it might be possible to accurately control the treatment depth by delivery of a specific light dose at the surface of the vessel lumen, this may be difficult to achieve in practice, due to the variations in tissue optical properties as well as the difficulty in accurately controlling the light level at all surfaces when using intravascular light. Furthermore, drug uptake will vary within the target treatment zone (even for the same tissue type) and the optical properties of the target tissue will vary between patients. These various factors will lead to significant practical limitations associated with variations in treatment depth, especially for wavelengths of 630 nm and greater. In practice, some regions in the target treatment area will receive an insufficient depth of treatment while others well outside the target treatment area will incur detrimental PDT effects.

Accordingly, there is a continuing need for a cardiovascular PDT treatment that delivers light to sufficiently penetrate into the target tissue, while simultaneously preventing the light from significantly penetrating through the tissue surrounding the target area.

SUMMARY OF THE INVENTION

The present invention involves excitation of photosensitizer drugs for treatment of cardiovascular occlusions using wavelengths selected to improve efficacy and safety over previous approaches. Through the use of wavelengths in the 390–610 nm range, there is minimal surrounding tissue damage and simultaneously a very significant PDT effect is achieved within the vessel which is the target of the treatment. Selection of the particular range of wavelengths is based on the scattering properties of tissue and the detailed absorption spectrum of hemoglobin and the critical role they play in light penetration in tissue. Absorption and scattering preferably prevents light from penetrating as deeply as with wavelengths in the red/infrared portion of the spectrum. In particular, at wavelengths in the 390–610 nm region, the optical penetration depth is comparable to the desired depth of treatment in cardiovascular applications of PDT. This in turn provides a means to eliminate many of the disadvantages that have been identified above for red or infrared light. Within the spectral region of 390–610 nm, the region of 440–610 nm is preferred when using devices that provide less efficient blood elimination or when a deeper depth of treatment is desired. This more restricted range is based on the fact that these wavelengths are on the long wavelength side of the Soret band for hemoglobin, thus there is not the severe attenuation by blood that exists for the shorter wavelengths. This method thereby allows sufficient penetration to treat thicker vessels to the desired depth in a reasonable time. This technique is applicable to all photosensitizers with sufficient absorption in this wavelength region. Here, sufficient absorption means an absorption coefficient high enough to allow treatment within a clinically relevant time period using available laser sources and allowable drug doses. This invention applies to, but is not limited to, photosensitizers of the following classes: texaphyrins, benzoporphyrin derivatives (including Visudyne), azaporphyrins, phthalocyanines, purpurins, Rose Bengal, xanthenes, porphycyanines, isomeric porphyrins, pentaphyrins, sapphyrins, phlorins, benzochlorins, hypericins, anthraquinones, rhodanols, barbituric acid derivatives, expanded porphyrins, dipyrromethenes, coumarins, azo dyes, acridines, rhodanine, azine derivatives, tetrazolium derivatives, safranines, indocyanines, indigo derivatives, indigo triazine derivatives, pyrrole derived macrocyclic compounds, naturally occurring or synthetic porphyrins, naturally occurring or synthetic chlorines, naturally occurring or synthetic bacteriochlorins, naturally occurring or synthetic isobacteriochiorins, naphthalocyanines, phenoxazine derivatives, phenothiazine derivatives, chaloorganapyrylium derivatives, triarylmethane derivatives, rhodamine derivatives, fluorescein derivatives, verdin derivatives, toluidine blue derivatives, methylene blue derivatives, methylene violet derivatives, nile blue derivatives, nile red derivatives, phenazine derivatives, pinacyanol derivatives, plasmocorinth derivatives and indigo derivatives (included in this list is any combination of these photosensitizers as well as these photosensitizers in combination with other chemical substances).

The preferred method would include photodynamic treatment of cardiovascular indications associated with occlusions of a blood vessel. This method involves the administration of a photosensitizer drug, either locally or systemically, and the delivery of intravascular light at an activation wavelength within the range of about 390 to about 610 nm such that the molar extinction coefficient of the drug at the activation wavelength is a least $1000 \text{ L cm}^{-1} \text{ M}^{-1}$.

BRIEF DESCRIPTION OF THE FIGURES

To facilitate further discussion of the invention, the following drawings are provided in which:

FIG. 9 is a chart demonstrating data obtained when treating rat carotid arteries using the method of the present invention;

FIG. 10 is chart demonstrating data obtained when treating rat carotid arteries using the method of the present invention and a wide range of PDT photosensitizing agents excited using the method of the present invention;

Figure 1:
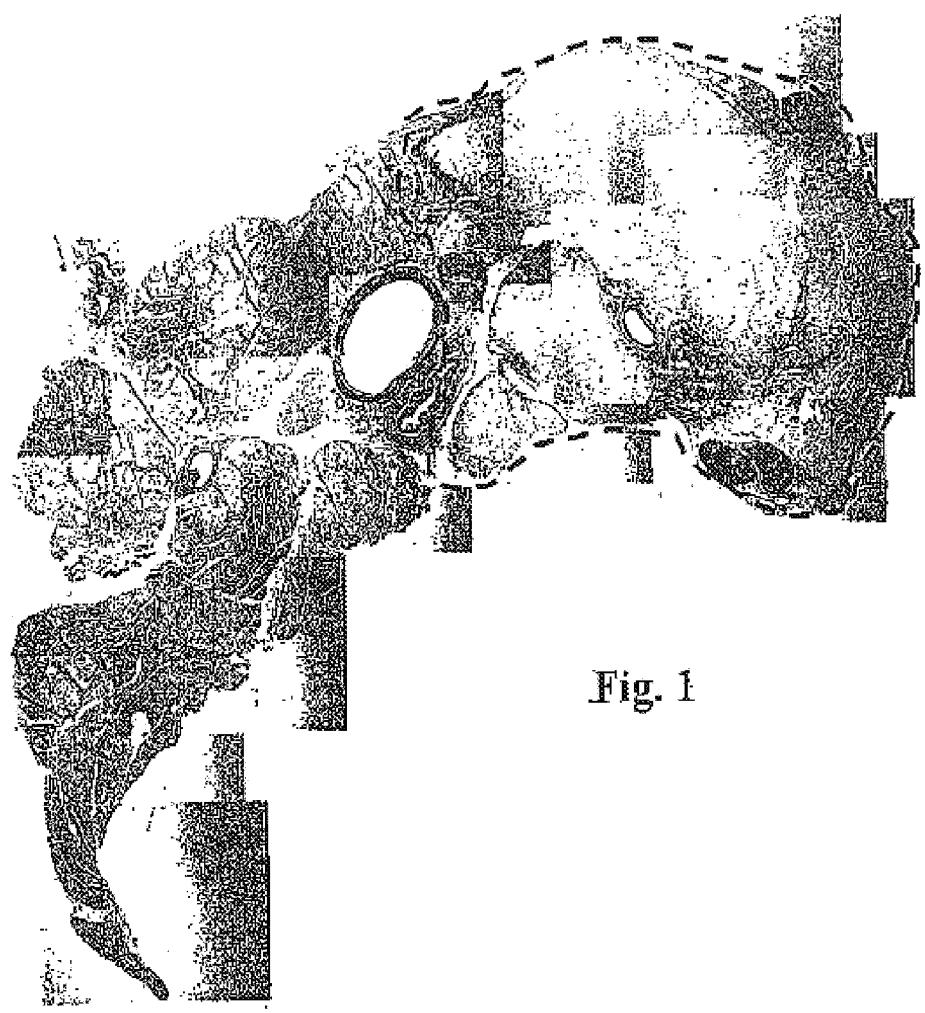
FIG. 1 is a low magnification image of a histological cross section of tissue taken from the throat region of a rat 3 days after it received PDT treatment using MV6401 and intravascular red light in the carotid artery (approximately 664 nm) delivered approximately 4 hours after drug injection, the dashed lines indicate the region of surrounding tissue damage.

These figures are for illustrative purposes only and should not be used to limit the scope of the claims.

DETAILED DESCRIPTION

The present invention provides a method for PDT treatment to inhibit, stabilize or reduce occlusions in the cardiovascular system by exciting photosensitizer drugs using intravascular light at a wavelength in the range of 390–610 nm. While investigators in the PDT field have consistently pointed out the advantages of using red/infrared light excitation, our results, while inconsistent with those viewpoints and unexpected, indicate that alternative wavelengths which are less penetrating will provide an improved method of treatment. The previous approach of using red/infrared wavelengths was based in part on taking advantage of the fact that the attenuation of light by tissue and blood reaches a minimum in the red/infrared part of the spectrum. However, we have discovered that, in direct contrast to this view, wavelengths outside this red/infrared spectral region are optimal for PDT-based cardiovascular treatments. While in theory, wavelengths in the mid-infrared could be used, we have found that the most effective wavelengths are those coincident with spectral regions of significant absorption by hemoglobin, in particular, wavelengths in the 390–610 nm range. This choice of wavelength range is based on the objective of providing a practical, safe and effective PDT treatment. Wavelengths less than 390 nm are in the ultraviolet portion of the spectrum. Such wavelengths have several drawbacks including absorption by other chrorpophores within tissue, potential for mutagenicity, lack of convenient light sources and tendency to cause light-induced damage of optical components. In the case of 610 nm, this wavelength corresponds to the onset of strong absorption by hemoglobin in blood, as hemoglobin has a relatively strong absorption for light having wavelengths less than approximately 610 nm. Therefore, by using excitation sources having wavelengths of 610 nm or shorter, one may take advantage of hemoglobin absorption to limit the PDT treatment to the target treatment zone. This approach appears to limit the degree of surrounding tissue damage to an acceptable level and simultaneously provides a significant PDT treatment in the target tissue, which was not practical with the approach of the prior art. Furthermore, to be effective, the preferred method uses this concept with photosensitizers having relatively strong absorption (greater than 1000 L $cm^{-1}$ $M^{-1}$). Photosensitizers having absorption coefficients less than this cannot be efficiently excited, resulting in the need to use high light irradiances, high light doses or high drug doses. High light irradiances can lead to thermal injury while high light doses require long treatment times and high drug doses raise the prospect of drug related toxicities. An advantage of PDT photosensitizers over other photoactive molecules, such as psoralens, is their absorption spectra. Specifically, PDT photosensitizers typically have relatively strong absorption features within this ideal spectral range that allow them to be efficiently excited using wavelengths within the range of 390–610 nm. Furthermore, PDT photosensitizers are not believed to significantly penetrate the cell nucleus, thereby avoiding any questions of treatment related mutagenic effects as have been raised with alternative therapies, such as psoralen based therapies.

Another benefit provided by this invention is a self-protection feature provided by hemoglobin in surrounding critical tissues. In peripheral arteries, much of the tissue that one would prefer to avoid damaging is the skeletal muscle surrounding the tissue. However, an even more critical situation exists in the case of coronary cardiovascular PDT treatments. There the vessel being treated is in very close proximity to surrounding myocardial tissue. In fact, in many cases the artery is directly adjacent to the myocardium. It is difficult to envision a situation where the complete PDT treatment can be elicited in the vessel wall as desired, without treating the myocardium lying directly adjacent to the vessel. However, the invention disclosed here provides an effective solution to this problem. In particular, both skeletal muscle and myocardial tissue contain high levels of hemoglobin as well as similar light absorbing chromophores. When irradiated with wavelengths greater than 610 nm, these tissues allow significant penetration of the light, which would lead to unacceptable PDT-related damage if the tissue contains a photosensitizer drug. On the other hand, when irradiated with wavelengths within the 390–610 nm region as disclosed here, the hemoglobin in these tissues provides a self-protective effect. In other words, by using the wavelengths disclosed here, we have found that we have created a situation in which these tissues are self-protected from undesired PDT effects, thereby improving safety and efficacy over that achievable with the prior art.

In summary, excitation of PDT photosensitizers using light within the 390–610 nm spectral range has at least the following advantages over the previous art: (1) absorption by hemoglobin significantly limits light propagation in surrounding tissue, thereby providing a means for protecting surrounding tissue from undesired PDT treatment, (2) light-induced and treatment-induced mutagenic effects are negligible, (3) scattering of light by tissue is sufficiently high to significantly limit the treatment depth to the target zone, (4) PDT photosensitizers have sufficiently high absorption in this wavelength range to allow them to be efficiently excited, and (5) practical light sources and delivery devices can be fabricated for this wavelength range. This combination of factors is a significant advance over the prior art.

Using these considerations, photosensitizers that possess significant optical absorption in the 390–610 nm range may be used to provide a previously unachievable selective PDT treatment for cardiovascular indications. Using excitation sources in this wavelength range, we have demonstrated in rat, rabbit and swine arteries that effective treatment depths can be obtained with these shorter wavelengths of light, while minimizing damage to underlying tissue. On the other hand, using these same animal species, results show that wavelengths greater than this are not the preferred treatment. This result was unexpected based on the selectivity characteristics of photosensitizers and the spatial falloff in light dose provided by cylindrical or point sources. Furthermore, this technique may be employed with a range of photosensitizers, even those not excited near their absorption maxima, as long as the absorption coefficient is reasonably high. Thus, the activation of such popular photosensitizers as lutetium texaphyrin (LuTex), BPD-MA, MACE, CASPc, SnET2, and pheophorbide PH-II26 with red/infrared light is not the optimal means of providing PDT based therapy for cardiovascular indications.

This invention may require removal of blood from the region between the light delivery device and the target tissue. For devices in which a limited amount of blood remains in this region or for which moderately deep treatment is desired, excitation in approximately the 440–610 nm range is preferred due to the relatively higher absorption by blood than occurs at shorter wavelengths. Specifically, wavelengths of approximately 440 nm and greater are on the long wavelength side of the Soret band for hemoglobin, such that for these wavelengths there is not the severe attenuation by blood that exists at shorter wavelengths. On the other hand, for devices that provide very efficient removal of blood, all wavelengths in the 390–610 nm range are effective.

This technique is applicable to all photosensitizers with sufficient absorption in this wavelength region. Here, sufficient absorption means an absorption coefficient high enough to allow treatment within a clinically relevant time period using available laser sources and allowable drug doses. The preferred value of the molar extinction coefficient at the treatment wavelength is about 1000 L cm$^{-1}$ M$^{-1}$ or greater. Compounds meeting these criteria include, but are not limited to, the following list of chemical classes, their derivatives and combinations of these: texaphyrins, benzoporphyrin derivatives (including Visudyne), azaporphyrins, phthalocyanines, purpurins, Rose Bengal, xanthenes, porphycyanines, isomeric porphyrins, pentaphyrins, sapphyrins, phlorins, benzochlorins, hypericins, anthraquinones, rhodanols, barbituric acid derivatives, expanded porphyrins, dipyrromethenes, coumarins, azo dyes, acridines, rhodanines, azine derivatives, tetrazolium derivatives, safranines, indocyanines, indigo dyes, triazine derivatives, pyrrole derived macrocyclic compounds, naturally occurring or synthetic porphyrins, naturally occurring or synthetic chlorines, naturally occurring or synthetic bacteriochlorins, naturally occurring or synthetic isobacteriochlorins, naphthalocyanines, phenoxazine derivatives, phenothiazine derivatives, chaloorganapyrylium derivatives, triarylmethane derivatives, rhodamine derivatives, fluorescein derivatives, verdin derivatives, toluidine blue derivatives, methylene blue derivatives, methylene violet derivatives, nile blue derivatives, nile red derivatives, phenazine derivatives, pinacyanol derivatives, plasmocorinth derivatives and indigo derivatives.

In contrast to the above classes of photosensitizers, psoralens have also been used in the inhibition of restenosis in animal models. These molecules have strong absorption in the ultraviolet portion of the spectrum, but minimal absorption at longer wavelengths. In particular, they have no Q-band absorption features. Specific application of these drugs for use in inhibition of restenosis are illustrated in March et al. U.S. Pat. No. 5,116,864 and Deckelbaum et al. U.S. Pat. No. 5,514,707. In the approach described in March, the photosensitizer is excited in the ultraviolet region of the spectrum to take advantage of the relatively high absorption in that region. While theoretically possible, this approach has several drawbacks as has been pointed out by Deckeibaum. These drawbacks include the mutagenic nature of ultraviolet light and the limited penetration of ultraviolet light. To avoid these drawbacks, Deckelbaum discloses a method of exciting psoralens in the blue portion of the spectrum, on the long wavelength side of the psoralen absorption peak.

The approach suggested by Deckelbaum is relatively inefficient because there is negligible absorption at this wavelength relative to its Soret band peak value. The primary impact of this lowered efficiency is the need for relatively high drug and/or light doses. As is known, use of high drug doses can lead to various drug-related toxicities. Similarly, use of high light doses results in long treatment times and/or the need to use high irradiances, both of which can result in light-related damage to the vessel.

Within the 390–610 nm range, the wavelength can be chosen to optimize the treatment parameters for the given indication. In coronary treatments it is important to avoid inadvertent PDT treatment of such critical tissues as lung and myocardium. In such cases, it is further desirable to utilize the shorter wavelength portion of the 390–610 nm spectrum, in particular those wavelengths corresponding to blue and green. On the other hand, peripheral vessels are often thicker, requiring a more penetrating treatment. Furthermore, the tissues surrounding peripheral vessels are typically not as critical. Therefore, in peripheral vessels the longer wavelength components of the 390–610 nm spectral range may be preferable. In such situations, depending on the desired depth of treatment and the light delivery device, wavelengths corresponding to the green and yellow are optimal. It is important to note that this technique allows one to easily adjust the treatment depth for a single photosensitizer by tuning the wavelength, as long as the extinction coefficient exceeds about 1000 L cm$^{-1}$M$^{-1}$ for that wavelength. This approach is significantly different than the prior art, in which it has almost always been the case that photosensitizers are excited near a local maximum in the absorption spectrum. However, this is not necessary and it may be advantageous to excite at other wavelengths. This is possible because the PDT photosensitizers listed above tend to have broad absorption profiles, making them amenable to this scheme.

A further advantage of this scheme is the selective treatment of tissues that do not contain significant levels of hemoglobin and to avoid treating those tissues that do contain hemoglobin. For example, muscle fibers tend to contain significant blood levels due to their high oxygen demands. One example here is skeletal muscle, while an even more important example is myocardium. Both of these contain significant levels of hemoglobin and should be shielded from the PDT treatment. However, since red/infrared light is not strongly absorbed by hemoglobin, these wavelengths readily penetrate such blood-containing tissues to excite the PDT photosensitizer contained in them. This is a major safety concern in PDT, especially for such tissues as myocardium. For example, myocardium can be located directly adjacent to coronary arteries, requiring very high selectivity in order to provide a safe PDT treatment. However, by utilizing wavelengths in the 390–610 nm range this shortcoming is largely avoided.

This invention provides improved safety and efficacy over previous approaches that use longer wavelengths and rely solely on drug selectivity. An additional advantage of this method is that it allows the use of photosensitizers that have little or no selectivity in uptake, yet have other positive characteristics. In one aspect, the method involves administering a PDT drug to a patient using either systemic or local drug delivery and allowing the agent to be taken up within the target blood vessel, then delivering intravascular light using a light delivery device that substantially eliminates blood from the region between the light delivery device and the tissue to be treated. One method is to deliver this excitation at a wavelength for which the molar extinction coefficient of the PDT agent has a value of about 1000 L cm$^{-1}$ M$^{-1}$ or higher.

For either type of drug delivery, some amount of delay may be imposed between the time of drug delivery and light delivery to allow the drug to be efficiently taken up within the target tissue/cell type area. The time for the photosensitizer drug build-up in the target area varies depending on the target area as well as the agent; however, it is generally in the range of several minutes to up to 48 hours, depending on the particular photosensitizer drug, its method of delivery and its formulation. However, regardless of the localizing features of the drug, the PDT effect can be localized appropriately through selection of the proper wavelength in combination with blood exclusion as is being outlined here.

Once the photosensitizer drug is delivered, the target area is exposed to intravascular phototherapeutic light radiation having a wavelength of between approximately 390 and 610 nanometers to excite the photosensitizer drug. For example, the distal portion of an optical fiber, which may include a diffusing element, is placed interstitially within a patient near or in a target tissue of interest. A source of optical radiation generating the treatment light is coupled to the proximal end of the optical fiber. For example, a diode laser, an argon laser, a dye laser, a solid state laser such as Nd:YAG, or any other suitable light source capable of producing light at a suitable wavelength within the 390–610 nm range is attached using appropriate couplers to the proximal end of the light delivery optical fiber. The light from the laser may be coupled and focused into the proximal end of the light delivery optical fiber using, for example, a conventional fiber termination assembly. The application of therapeutic light to the target tissue will activate the photosensitizer drug to provide the desired PDT effect. A light dose corresponding to a total treatment time of 1–5 minutes is generally preferred, although this invention applies to both longer and shorter treatment durations.

The feasibility of this concept for cardiovascular indications was originally demonstrated in a rat carotid artery using intravascular light and systemic administration of the photosensitizer drug, MV6401. The light delivery device had an angioplasty-style balloon at its distal end to exclude blood from the region between the balloon and the vessel wall. The central lumen of this catheter was designed to allow passage of an optical fiber having a diffuser at its distal end. The fiber was positioned such that the diffusing section was centered within the light delivery balloon, thereby providing intravascular light delivery with minimal absorption by blood. Excitation was typically provided by a laser source at the proximal end of the device, which was focused on the proximal end of the fiber-optic diffuser. Typical wavelengths used were 405 nm, 407 nm, 413 nm, 436 nm, 442 nm, 458 nm, 514 nm, 532 nm, and the general range of 570–610 nm.

The surgery was performed by doing a cutdown to allow access to the right femoral artery, followed by insertion of the light delivery catheter. The catheter was then passed up through the iliac and abdominal aorta, through the aortic arch and into the left carotid artery. Once in place, the balloon was inflated to approximately 1 atmosphere using a standard angioplasty inflation device. This caused the balloon to expand to the diameter of the artery, while still allowing the pressure to be kept low enough to prevent significant over-stretch of the artery. This method effectively eliminated the blood from the intervening region between the balloon and the artery.

Prior to this surgery, the rats were injected with a photosensitizer drug to allow uptake of the drug into the target tissues. Uptake of the drug within the target tissues was confirmed by fluorescence microscopy and high pressure liquid chromatography (HPLC). Specifically, these results indicated that the photosensitizer drug used in these experiments was more strongly localized in the target tissue. These results were similar to results cited by others. However, when excited with light having a wavelength of 665 nm, there was a significant amount of damage to surrounding tissues. This result is most likely due to a combination of one or more of the following factors: much deeper penetration of the light at 665 nm, less than complete selectivity in drug uptake, and higher sensitivity of surrounding tissues to the PDT effect. However, by using wavelengths within the range disclosed herein, this trauma was significantly reduced. Furthermore, acellularity was induced within the medial wall. Induction of acellularity is believed to inhibit intimal hyperplasia, the most common cause of restenosis in post-angioplasty patients. This result indicated that the treatment reached the desired threshold dose in the target tissue, while simultaneously sparing damage to the surrounding tissue that was not the target of the treatment. To our knowledge, such efficacy using intravascular light has never been achieved previously with PDT. Unlike the case with red/infrared excitation, here the animals demonstrated no clinical evidence of an adverse PDT treatment effect. Similarly, when histology was performed, animals treated with red/infrared light showed significant PDT effects in surrounding tissues but little or no PDT treatment effects in the target tissue. This was notable since the target tissues appeared to contain a higher drug concentration and they were also located closest to the light source. However, histology performed on animals treated with the general range of wavelengths disclosed here showed the opposite effect. Namely, a significant PDT effect has been seen in the target tissues with very minimal PDT effect in the surrounding tissue.

Following this demonstration, we performed similar experiments using commonly available photosensitizers (BPD, LuTex, Rose Bengal). As was the case with MV6401, here acellularity was induced in the medial wall while largely sparing the surrounding tissue. Again, to our knowledge, this is the first time such a desired biological response has been demonstrated with these compounds using intravascular excitation.

Figure 2:
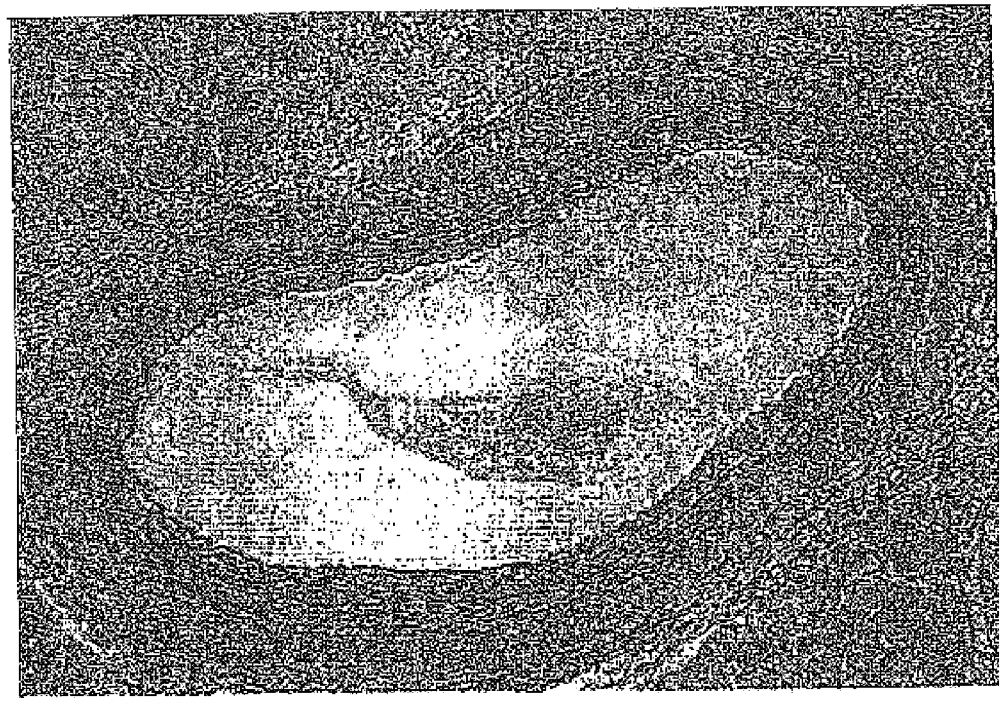
FIG. 2 is a close-up image of the artery in FIG. 1 in which the intravascular PDT light delivery device was placed.
Figure 3:
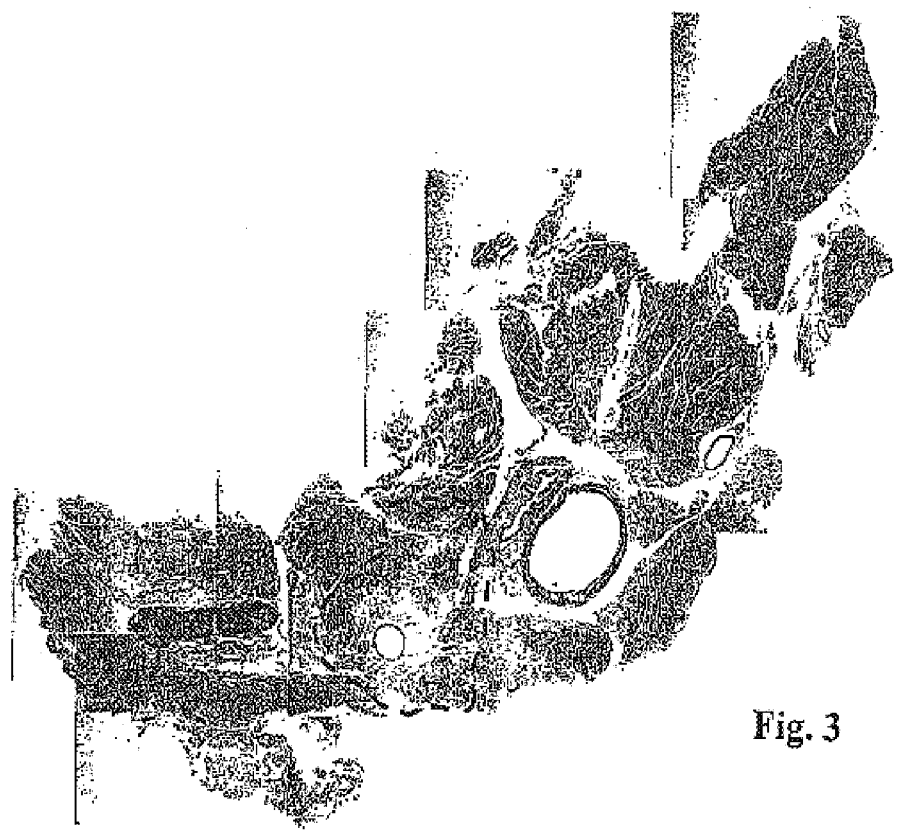
FIG. 3 is a low magnification image of a histological cross section of tissue taken from the throat region of a rat 3 days after it received PDT treatment using MV6401 and intravascular blue light (approximately 458 nm) in the carotid artery delivered approximately 4 hours after drug injection, the dashed lines indicate the region of surrounding tissue damage.
Figure 4:
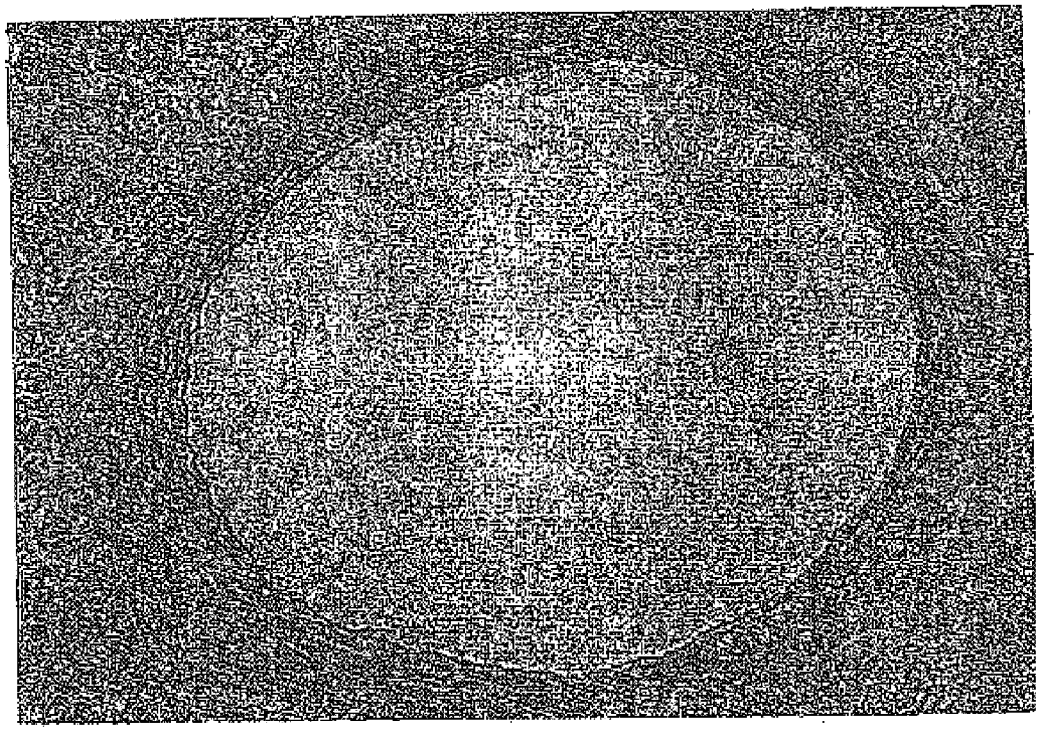
FIG. 4 is a close-up image of the artery in FIG. 3 in which the intravascular PDT light delivery device was placed.

FIG. 1 is a low magnification image of a tissue cross section taken from the throat of a rat that has received PDT therapy using intravascular red light. Treatment parameters were: 0.1 $\mu$mol/kg of the photosensitizer drug MV6401 using systemic administration with light treatment at 4 hours post drug administration using a wavelength of 665 nm and a light dose of 100 J/cm$^2$ using a bare fiber diffuser. (A bare fiber diffuser was used here since complete blood elimination is not necessary at this wavelength due to the relatively high penetration of light through blood at this wavelength.) The animal was sacrificed 4 days after the PDT treatment, the throat section was harvested, embedded and stained using hematoxylin and eosin (H&E). This image demonstrates significant PDT-induced inflammation and necrosis in the tissue surrounding the vessel. This level of surrounding tissue damage was correlated with unacceptable clinical symptoms. Furthermore, even with this level of surrounding tissue damage, there were still viable cells present in the target vessel wall. This result is illustrated in FIG. 2 which is a high magnification image of the treated artery in FIG. 1. These results demonstrate that while this drug appears to be taken up preferentially in the target vessel tissue and this tissue is closest to the light emitting diffuser such that it receives the highest incident light level, the target tissue is not significantly affected by the PDT treatment. On the other hand, the surrounding tissue, which is not the target of treatment, is significantly affected, even though it demonstrated less drug-related fluorescence and was farther from the light diffusing element. FIG. 3 is a similar low magnification image of tissue collected from the throat region of a rat that received PDT treatment using intravascular light, except in this case we excited the drug using blue light. Treatment parameters were: 2 μmol/kg of the photosensitizer drug MV6401 using systemic administration with light treatment at 4 hours post drug administration using a wavelength of 458 nm and a light dose of 100 J/cm$^2$ using a light delivery device that included a balloon to eliminate blood from the region between the intravascular light delivery fiber and the vessel wall. A balloon was placed around the fiber light diffuser here since it is important to eliminate blood at these wavelengths due to the optical absorption of hemoglobin. Furthermore, a significantly higher drug dose was used here to help compensate for the fact that this drug absorbs much more strongly at red wavelengths than the blue. The animal was sacrificed 5 days after the PDT treatment, the throat section was harvested, embedded and stained using hematoxylin and eosin (H&E). This image demonstrates minimal PDT-induced inflammation and necrosis and in this case these effects do not encompass a large region of tissue but rather are localized around the treated artery. This level of surrounding tissue damage was found to be well tolerated by the animals as they displayed no adverse clinical symptoms. Furthermore, this surrounding tissue damage appeared to resolve with time, whereas when red light was used the animals generally had to be sacrificed due to the severity of their clinical symptoms. In addition to this, we found that in contrast to the result observed with red light, with blue light complete acellularity was induced in the vessel wall. This result is illustrated in FIG. 4 which is a high magnification image of the treated artery in FIG. 3. Notice that here the artery is almost entirely acellular, whereas in the red light case of FIG. 2, the artery is completely cellular (cells are identified as the dark elliptical spots located within the cell wall). While a very limited number of cells appear to remain in the blue light treated areas, these have the appearance of injured cells and are not likely to contribute significantly to proliferation. This is an important point since it indicates that unlike the above case, a significant PDT treatment effect has been induced in the vessel wall. More importantly, such acellularity correlates with the inhibition of restenosis. In fact, it is widely believed that viable smooth muscle cells in the media and adventia are the source of the proliferating cells that are responsible for restenosis. By eliminating these cells, while leaving a mechanically viable vessel and minimal surrounding tissue damage, we have identified a practical means for PDT treatment of such occlusive events using intravascular light. Previous attempts have not identified such an approach because they have either used external illumination or they have not used sufficiently high doses to elicit the desired PDT response.

Figure 5:
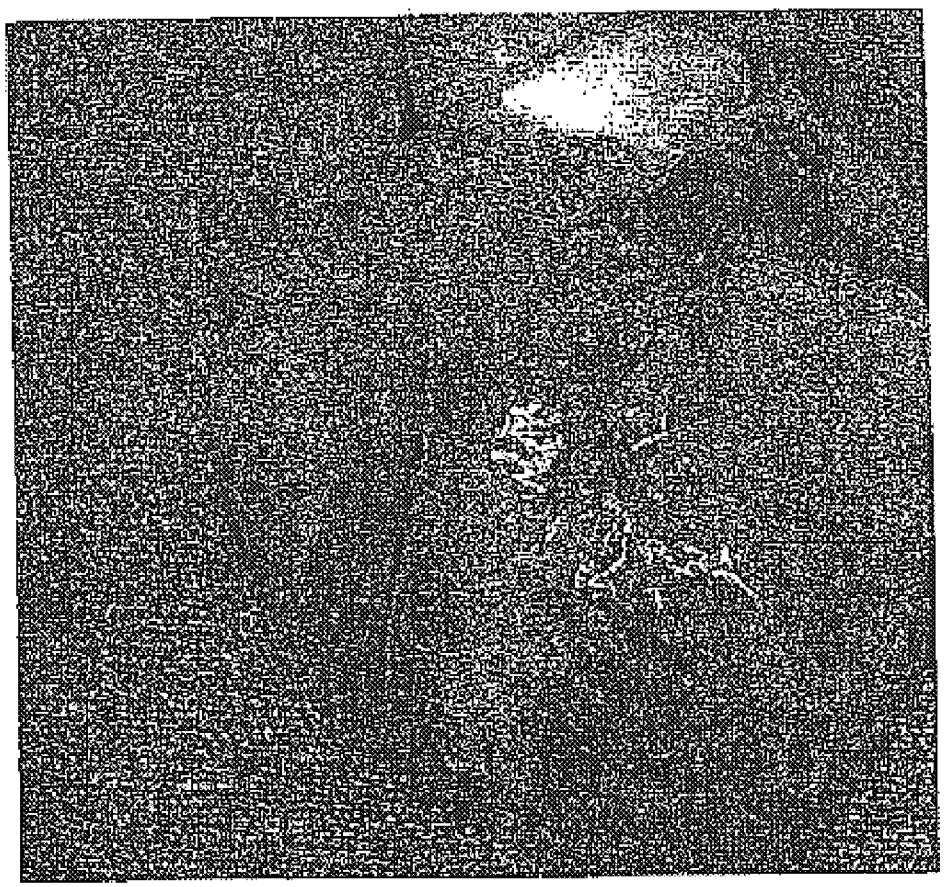
FIG. 5 is an image of a porcine heart harvested at 3 days after receiving PDT in a coronary artery using MV6401 and intravascular red light (approximately 664 nm)
Figure 6:
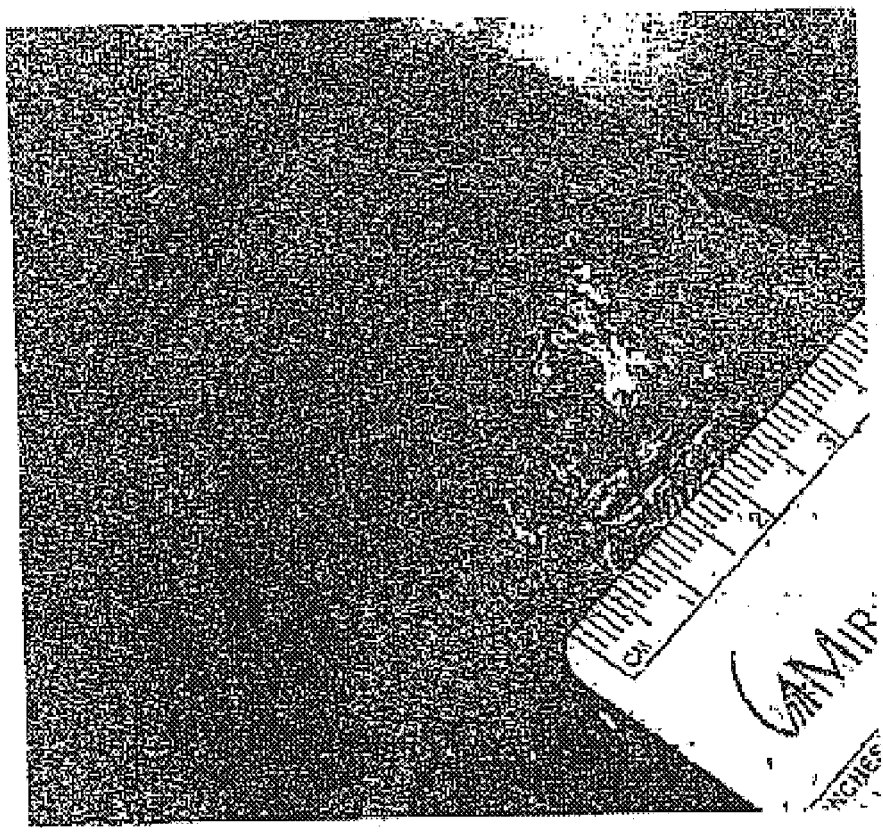
FIG. 6 is an image of a porcine heart harvested at 3 days after receiving PDT in a coronary artery using MV6401 and intravascular blue light (approximately 458 nm)
Figure 7:
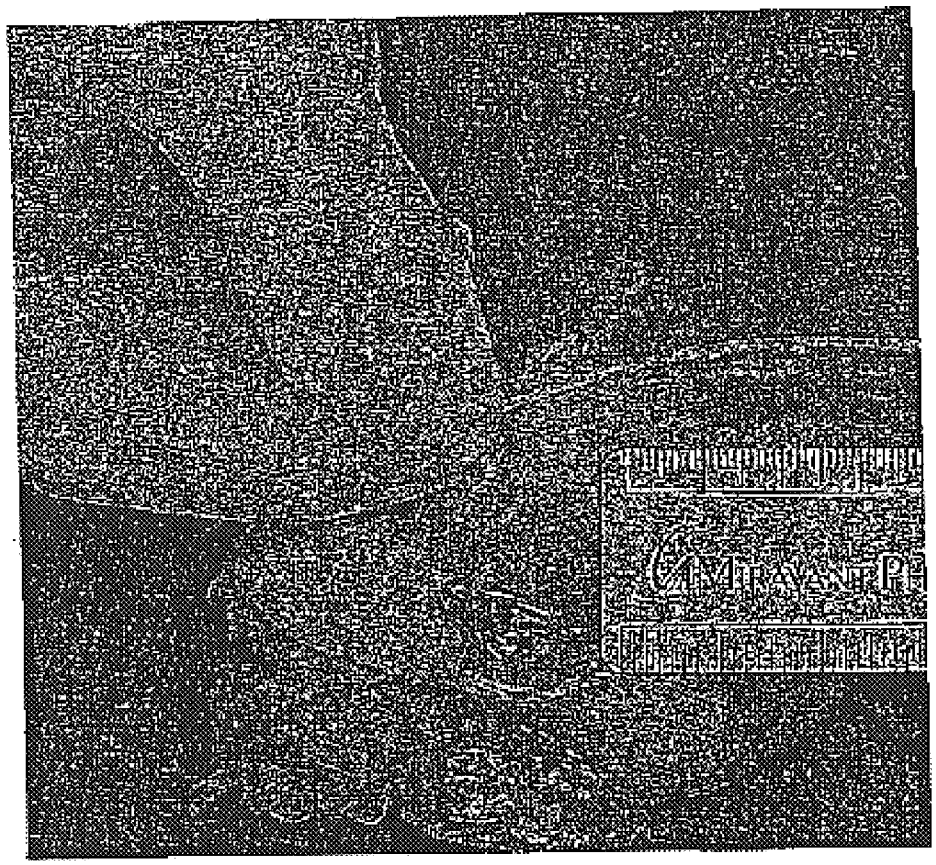
FIG. 7 is an image of a porcine heart harvested at 3 days after receiving PDT in a coronary artery using MV6401 and intravascular green light (approximately 532 nm)

The above result translates to other, more significant animal models. As an example, in FIG. 5 we present an image of a heart harvested from a swine following PDT treatment using intravascular red light (665 nm). It is important to note the unacceptable PDT-induced damage as evidenced by the hemorrhage extending into the myocardium. In contrast, FIGS. 6 and 7 are images of swine hearts taken from animals following intravascular PDT treatment using blue light (458 nm) and green light (532 nm), respectively. In this case, the PDT-induced damage is confined to the immediate area surrounding the vessel, with minimal damage to the myocardium. These results have been confirmed using histology similar to that done with the rats described above. In fact, we have found that complete acellularity can be achieved within the vessel media and adventia with surrounding tissue damage of the order seen in FIG. 6 and 7. Such acellularity could not be achieved using red light since the damage to surrounding tissues required that these studies be terminated. Even at such high PDT doses that resulted in severe adverse clinical reactions, insignificant acellularity was induced in the media or adventia of the vessel.

Figure 8:
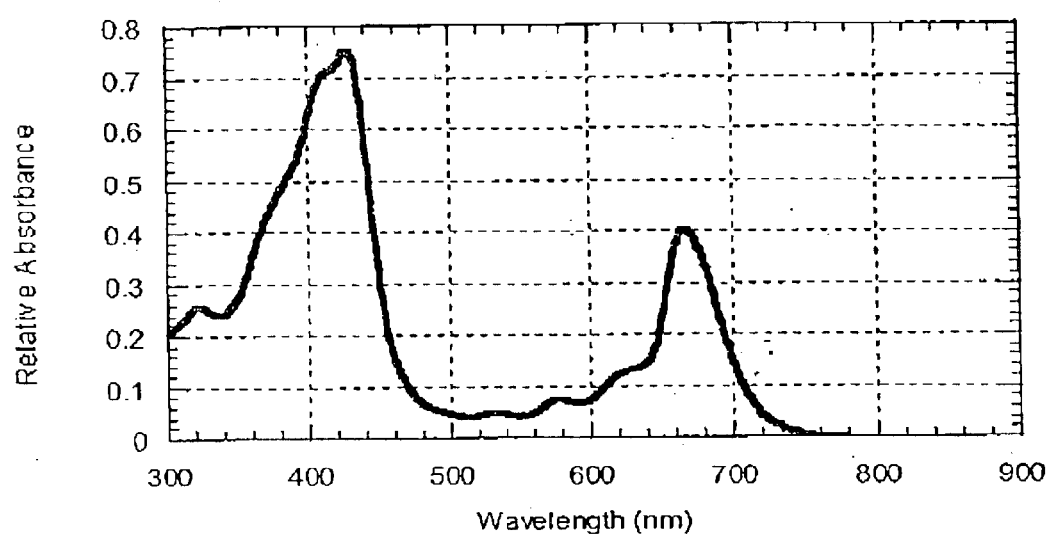
FIG. 8 is a graph showing the relative optical absorption spectra of MV6401 in an egg yolk phospholipid formulation.

FIG. 8 is an image of the absorption spectrum of the photosensitizer MV6401, demonstrating that this drug absorbs most strongly near 425 nm and 665 nm, with much smaller absorption near 458 nm and 532 nm. However, even this lowered absorption is in excess of 1000 L cm$^{-1}$ M$^{-1}$ which is sufficient to provide an effective PDT response using reasonable light doses. While the above results were obtained using either 458 nm or 532 nm, other wavelengths throughout the range disclosed here can be used as well.

FIG. 9 presents data obtained when treating rat carotid arteries using various wavelengths (442, 458, 514, 532 and 665 nanometers) of intravascular light and the photosensitizer MV6401. In FIG. 9, the results are listed in the columns titled *Max. Accell.*, listing the acellularity measured in the section for which the acellularity was highest and *Sur. Tissue Damage*, listing the degree of surrounding tissue damage. To assess the degree of surrounding tissue damage, a qualitative scoring system was developed were 0 means no observable damage, 1 means observable but minor damage, 2 means significant damage that is observed near the artery as well as 1–2 artery diameters away from the artery, and 3 is surrounding tissue damage that generally completely encompasses the treated artery as well as extending several artery diameters away from the treated artery. The desired objective was to achieve significant acellularity with minimal damage to surrounding tissue. Results indicate that this can be effectively achieved with proper wavelength selection.

It is important to note that the results presented in FIG. 9 for excitation in the 390–610 nm spectral region were not unique to this particular drug. Rather, these results were typical of those obtained with a wide variety of photosensitizing agents. For example, in FIG. 10 we present results obtained with a variety of commonly used PDT agents. These data demonstrate that the method of this invention is quite general. In particular, it allows the effective use of photosensitizers that are not specifically selective to arterial tissue by achieving that selectivity by choice of light wavelength. It should also be noted that some PDT photosensitizers worked better than others, which is most likely a result of whether or not those drugs are taken up within the target tissues. In other words, by using the proper wavelength to provide a selective result, the desired result can be achieved with any photosensitizer that is taken up within the target tissue, regardless of how well it is taken up in surrounding tissues.

Figure 11:
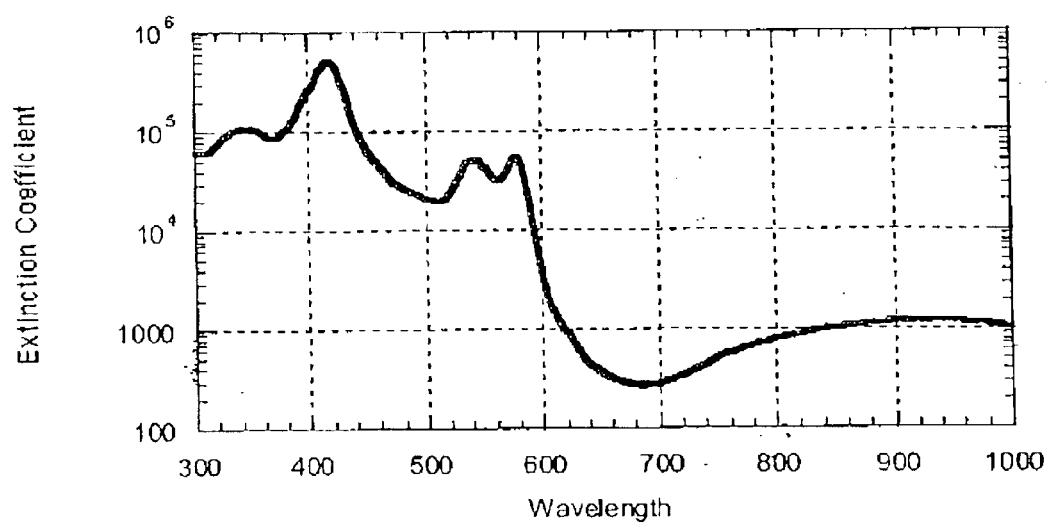
FIG. 11 is a graph illustrating the absorption spectrum of hemoglobin.
Figure 12:
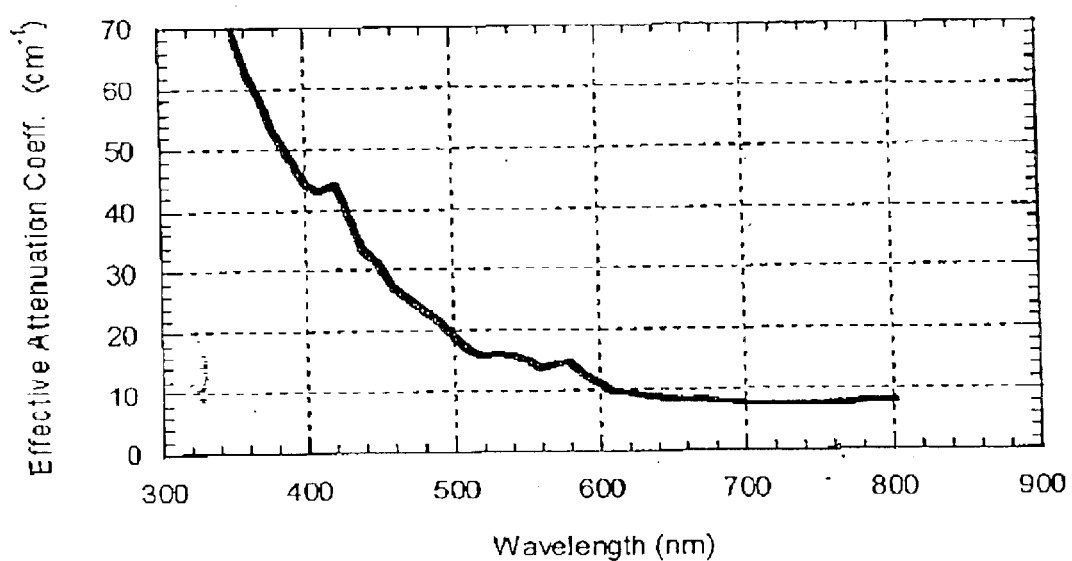
FIG. 12 is a graph illustrating the increase in the optical scattering coefficient of arterial tissue (aorta) as a function of wavelength.

Stated differently, the selectivity of the PDT effect is significantly enhanced relative to previous approaches when using this method. We hypothesize that this is due to the fact that for the 390–610 nm range of wavelengths, there is limited penetration due to tissue scattering and absorption. FIG. 11 illustrates the absorption spectrum of hemoglobin and FIG. 12 illustrates the effective attenuation coefficient measured in aorta tissue (A. A. Oraevsky, et al., Optical properties and energy pathways, Lasers Surg. Med., 12, 585–597, 1992). (This is mainly the result of scattering since there is minimal hemoglobin present in aorta tissue.) In the case of blood absorption, it is clear that for situations where a limited amount of blood is present or a deeper depth of treatment is desired, the general spectral range of 440–610 nm is preferable. On the other hand, when blood is very efficiently eliminated or a lesser depth of treatment is desired, the entire spectral range can be utilized.

Figure 13:
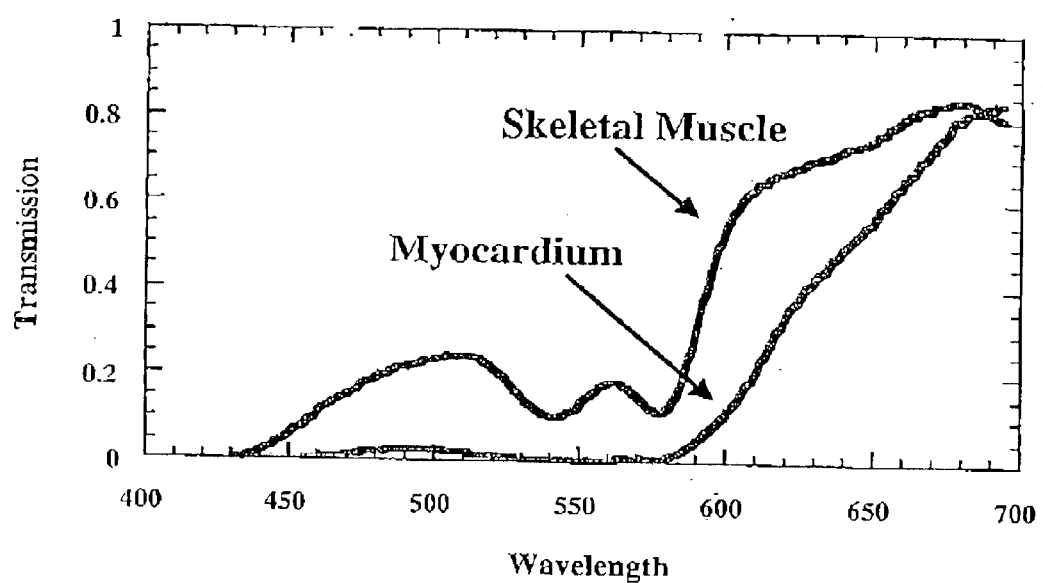
FIG. 13 is a graph showing the spectral transmission through 1 mm thick sections of bovine skeletal muscle and myocardium.

While the vessel wall, which is the target of the treatment, contains relatively low concentrations of hemoglobin, other surrounding tissues such as skeletal muscle and myocardium contain relatively high levels of hemoglobin. This provides a self-protection benefit if one uses wavelengths in the 390–610 nm range. An illustration of this effect is given in FIG. 13, which gives results obtained by measuring the spectral transmission through approximately 1 mm thick sections of bovine skeletal muscle and myocardium.

Figure 14:
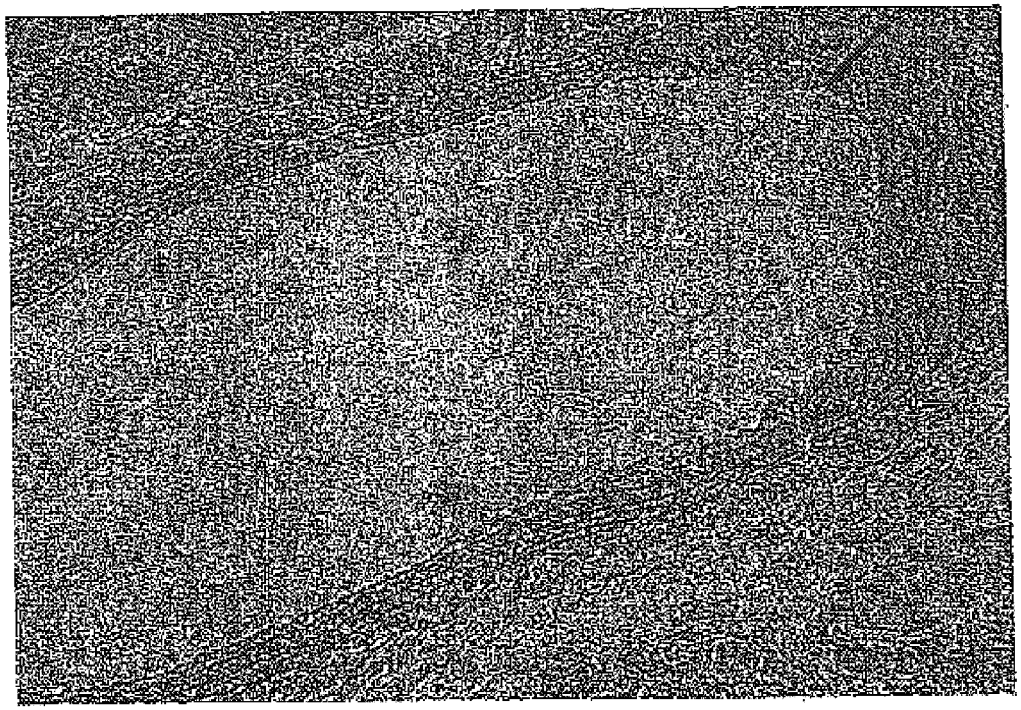
FIG. 14 is a close-up image of an H&E stained cross section of tissue taken from the throat region of a rat 3 days after it received PDT treatment using LuTex and intravascular blue light in the carotid artery (approximately 458 nm) delivered approximately 4 hours after drug injection.
Figure 15:
FIG. 15 is a close-up image of an H&E stained cross section of tissue taken from the throat region of a rat 3 days after it received PDT treatment using benzoporphyrin derivative (BPD/Visudyne®) and intravascular blue light in the carotid artery (approximately 458 nm) delivered approximately 2 hours after drug injection.

It is important to note that the art of this invention is not limited to specific drugs, but rather can be used to provide a practical means of intravascular PDT treatment of vessels using many popular photosensitizer drugs. As an example, FIGS. 14 and 15 present data obtained with LuTex and BPD, respectively. In each of these, the media is largely devoid of cells, indicating that PDT-induced acellularity has been achieved. In each of these cases, no animals displayed adverse symptoms consistent with our observation of minimal surrounding tissue damage. In fact, histological examination showed minimal evidence of PDT-induced damage in surrounding tissue with nearly complete acellularity within the media, very similar to the results achieved with MV6401.

The present invention: (1) eliminates the need for a highly selective drug by reducing the average treatment depth relative to that which results with red/infrared light, and (2) avoids the mutagenic effects associated with excitation using shorter wavelengths and/or psoralens, and (3) allows the depth of treatment to be controlled in a simple manner by varying the wavelength of light, and (4) provides a means for safe treatment by utilizing excitation wavelengths for which there is a self-protection benefit in critical surrounding tissues.

While the utility of the disclosed method has been demonstrated in the treatment of injured arteries as an example, it should not be construed that this method is limited to that application. The use of this method to treat other lesions, hyperproliferative cells or occlusive events within the cardiovascular system is an obvious extension of the invention.

It is understood that the following claims are intended to cover all generic and specific features of the invention described herein.

What is claimed is:

1. A method of PDT treatment of cardiovascular indications associated with occlusions of a blood vessel comprising the steps of:
    administering a photosensitizer drug other than psoralen compounds; and
    delivering intravascular photoactivating light to the blood vessel at an activation wavelength within the range of about 390 to 610 nm such that the molar extinction coefficient of the photosensitizer drug at the activation wavelength is at least 1000 L cm$^{-1}$ M$^{-1}$.

2. The method of claim 1 wherein the photosensitizer drug is texaphyrin or a derivative thereof.

3. The method of claim 2 wherein the photosensitizer drug is lutetium texaphyrin.

4. The method of claim 3 wherein the light is delivered at an activation wavelength within the range of about 457 to about 458 nm.

5. The method of claim 1 wherein the photosensitizer drug is a benzoporphyrin or a derivative thereof.

6. The method of claim 5 wherein the light is delivered at an activation wavelength within the range of about 457 to about 458 nm.

7. The method of claim 5 wherein the photosensitizer drug is Visudyne.

8. The method of claim 1 wherein the photosensitizer drug is a xanthene or a derivative thereof.

9. The method of claim 8 wherein the photosensitizer drug is Rose Bengal or a derivative thereof.

10. The method of claim 1 wherein the photosensitizer drug is azoporphyrin or a derivative thereof.

11. The method of claim 1 wherein the photosensitizer drug is a phthalocyanine or a derivative thereof.

12. The method of claim 1 wherein the photosensitizer drug is a naturally occurring or synthetic porphyrin or a derivative thereof.

13. The method of claim 1 wherein the photosensitizer drug is a pupurin or a derivative thereof.

14. The method of claim 1 wherein the photosensitizer drug is a naturally occurring or synthetic chlorin or a derivative thereof.

15. The method of claim 1 wherein the photosensitizer drug is a porphycyanine or a derivative thereof.

16. The method of claim 1 wherein the photosensitizer drug is an isomeric porphyrin or a derivative thereof.

17. The method of claim 1 wherein the photosensitizer drug is a pentaphyrin or a derivative thereof.

18. The method of claim 1 wherein the photosensitizer drug is a sapphyrin or a derivative thereof.

19. The method of claim 1 wherein the photosensitizer drug is a phlorin or a derivative thereof.

20. The method of claim 1 wherein the photosensitizer drug is a naturally occurring or synthetic bacteriochlorin or a derivative thereof.

21. The method of claim 1 wherein the photosensitizer drug is a benzochlorin or a derivative thereof.

22. The method of claim 1 wherein the photosensitizer drug is a hypericin or a derivative thereof.

23. The method of claim 1 wherein the photosensitizer drug is an anthraquinone or a derivative thereof.

24. The method of claim 1 wherein the photosensitizer drug is a rhodanol or a derivative thereof.

25. The method of claim 1 wherein the photosensitizer drug is a barbituric acid or a derivative thereof.

26. The method of claim 1 wherein the photosensitizer drug is an expanded porphyrin or a derivative thereof.

27. The method of claim 1 wherein the photosensitizer drug is a dipyrromethene or a derivative thereof.

28. The method of claim 1 wherein the photosensitizer drug is a coumarin or a derivative thereof.

29. The method of claim 1 wherein the photosensitizer drug is an azo or a derivative thereof.

30. The method of claim 1 wherein the photosensitizer drug is an acridine or a derivative thereof.

31. The method of claim 1 wherein the photosensitizer drug is a rhodanine dye or a derivative thereof.

32. The method of claim 1 wherein the photosensitizer drug is an azine dye or a derivative thereof.

33. The method of claim 1 wherein the photosensitizer drug is a tetrazolium dye or a derivative thereof.

34. The method of claim 1 wherein the photosensitizer drug is a safranine or a derivative thereof.

35. The method of claim 1 wherein the photosensitizer drug is an indocyanine or a derivative thereof.

36. The method of claim 1 wherein the photosensitizer drug is an indigo dye or a derivative thereof.

37. The method of claim 1 wherein the photosensitizer drug is a triazine dye or a derivative thereof.

38. The method of claim 1 wherein the photosensitizer drug is a pyrrole derived macrocyclic compound or a derivative thereof.

39. The method of claim 1 wherein the photosensitizer drug is a naturally occuring or synthetic isobacteriochlorin or a derivative thereof.

40. The method of claim 1 wherein the photosensitizer drug is a naphthalocyanine or a derivative thereof.

41. The method of claim 1 wherein the photosensitizer drug is a phenoxazine or a derivative thereof.

42. The method of claim 1 wherein the photosensitizer drug is a phenothiazine or a derivative thereof.

43. The method of claim 1 wherein the photosensitizer drug is a chaloorganapyrylium or a derivative thereof.

44. The method of claim 1 wherein the photosensitizer drug is a triarylmethane or a derivative thereof.

45. The method of claim 1 wherein the photosensitizer drug is a rhodamine or a derivative thereof.

46. The method of claim 1 wherein the photosensitizer drug is fluorescein or a derivative thereof.

47. The method of claim 1 wherein the photosensitizer drug is a verdin or a derivative thereof.

48. The method of claim 1 wherein the photosensitizer drug is touidine blue or a derivative thereof.

49. The method of claim 1 wherein the photosensitizer drug is methylene blue or a derivative thereof.

50. The method of claim 1 wherein the photosensitizer drug is methylene violet or a derivative thereof.

51. The method of claim 1 wherein the photosensitizer drug is nile blue or a derivative thereof.

52. The method of claim 1 wherein the photosensitizer drug is nile red or a derivative thereof.

53. The method of claim 1 wherein the photosensitizer drug is a phenazine or a derivative thereof.

54. The method of claim 1 wherein the photosensitizer drug is a pinacyanol or a derivative thereof.

55. The method of claim 1 wherein the photosensitizer drug is a plasmocorinth or a derivative thereof.

56. A method of PDT treatment of cardiovascular indications associated with occlusions of a blood vessel comprising the steps of:

administering a photosensitizer drug; and delivering a photoactivating light to the blood vessel with an intravascular light delivering device at an activation wavelength within the range of about 440 to 610 nm such that the molar extinction coefficient of said drug at the activation wavelength is at least 1000 L cm$^{-1}$ M$^{-1}$.

57. The method of claim 1 wherein the photosensitizer drug is a naturally occurring porphyrin induced by an amino-levulinic acid, an amino-levulinic acid ester, an amino-levulinic amide, or derivatives thereof.

58. The method of claim 1 wherein the intravascular photoactivating light is delivered approximately two minutes to forty-eight hours after the administration of the photosensitizer drug.

59. The method of claim 1 wherein the treatment stabilizes or causes a reduction in size of atherosclerotic vulnerable plaques that can result in vessel occlusion if left untreated.

* * * * *